United States Patent [19]

Surer et al.

[11] Patent Number: 5,399,360
[45] Date of Patent: Mar. 21, 1995

[54] PHARMACEUTICAL COMPOSITIONS

[75] Inventors: Hansruedi Surer; Aldo Riva, both of Bern, Switzerland

[73] Assignee: Sandoz Pharmaceuticals Corp., E. Hanover, N.J.

[21] Appl. No.: 105,532

[22] Filed: Aug. 11, 1993

Related U.S. Application Data

[63] Continuation of Ser. No. 901,455, Jun. 19, 1992, abandoned, which is a continuation of Ser. No. 791,843, Nov. 14, 1991, abandoned, which is a continuation of Ser. No. 463,566, Jan. 11, 1990, abandoned, which is a continuation of Ser. No. 258,306, Oct. 14, 1988, abandoned, which is a continuation of Ser. No. 64,412, Jun. 18, 1987, abandoned.

[30] Foreign Application Priority Data

Jun. 21, 1986 [DE] Germany ............... 36 20 830.2

[51] Int. Cl.⁶ ............................................. A61K 9/26
[52] U.S. Cl. .................... 424/469; 424/468; 424/470; 424/482; 514/324; 514/826; 546/202
[58] Field of Search ............ 424/469, 468, 470, 482; 514/324, 826; 546/202

[56] References Cited

U.S. PATENT DOCUMENTS

| | | | |
|---|---|---|---|
| 4,073,915 | 2/1978 | Martin | 514/826 |
| 4,419,352 | 12/1983 | Cox et al. | 514/291 |
| 4,797,286 | 1/1989 | Thakkar et al. | 424/456 |
| 4,798,725 | 1/1989 | Patel | 424/456 |
| 4,880,634 | 11/1989 | Speiser | 424/450 |
| 5,006,345 | 4/1991 | Lang | 424/467 |
| 5,069,911 | 12/1991 | Zuger | 424/469 |

FOREIGN PATENT DOCUMENTS

| | | |
|---|---|---|
| 1355537 | 6/1974 | United Kingdom . |
| 2154874 | 9/1985 | United Kingdom . |
| 2163957 | 3/1986 | United Kingdom . |

OTHER PUBLICATIONS

Schmidt-Redemann, et al, International Journal of Clinical Pharmacology, vol. 24, No. 9, pp. 496-498 (1986).
Julien Larose, et al, Biomedical Mass Spectrometry, vol. 10, No. 3, pp. 136-142 (1983).
Lavene et al, 1st European Congress of Biopharmaceuticals and Pharmacokinetics, vol. III, p. 296 (1981) (Abstract).
Hagers Handbuch der Pharmazeutischen Praxis, Springer-Verlag, p. 689 (1971).
Doelker et al, Pharma. Acta Helv., vol. 56, pp. 111-118 (1981).
Austria-Codex, Binder et al, pp. 1197 (1985).
British National Formulary, pp. 128-129 (Sep. 1989).

*Primary Examiner*—Thurman K. Page
*Assistant Examiner*—Robert H. Harrison
*Attorney, Agent, or Firm*—Robert S. Honor; Melvyn M. Kassenoff; Carl W. Battle

[57] ABSTRACT

A ketotifen pharmaceutical composition adapted for once-a-day oral administration e.g. based on a fat matrix.

8 Claims, 7 Drawing Sheets

PHARMACEUTICAL COMPOSITIONS

This is a continuation of application Ser. No. 07/901,455, filed Jun. 19, 1992, now abandoned, which in turn is a continuation of application Ser. No. 07/791,843, filed Nov. 14, 1991, now abandoned, which in turn is a continuation of application Ser. No. 07/463,566, filed Jan. 11, 1990, now abandoned which in turn is a continuation of application Ser. No. 07/258,306, filed Oct. 14, 1988, now abandoned, which in turn is a continuation of application Ser. No. 07/064,412, filed Jun. 18, 1987, now abandoned.

This invention relates to pharmaceutical compositions, particularly containing as an active agent 4-(1-methyl-4-piperidylidene)-4H-benzo[4,5]cyclohepta[1,2-b]thiophen-10(9H)-one, also known as ketotifen, and especially those which are sustained release or retard formulations.

Ketotifen is described in German Patent 2,111,071. It has anti-anaphylactic and anti-histamine properties and is useful, e.g. for the prophylaxis of asthma and treatment of allergieso Ketotifen is generally administered twice-a-day. Adults usually take a unit dose of 1 mg.

Little has been published in the patent and academic literature on formulations of ketotifen which would provide a satisfactory therapeutic effect on once-a-day administration of a unit dosage formulation.

After extensive research into the biopharmaceutical and physical properties of ketotifen and extensive testing of ketotifen retard compositions we have now provided a commercially acceptable once-a-day oral pharmaceutical composition containing ketotifen.

The pharmaceutical compositions of the invention provide for the first time a once-a-day administration of ketotifen. These pharmaceutical compositions are especially indicated for use in asthma prophylaxis. Asthma attacks occur unexpectedly and not infrequently in the very early morning.

Pharmaceutical compositions of the present invention provide an effective level of ketotifen over long periods, and will provide protection against such attacks.

The pharmaceutical compositions of the invention provide a sustained and high absorption of ketotifen. The fluctuations in the plasma levels of ketotifen observed on steady state administration of the pharmaceutical compositions are unexpectedly small. Administration of the pharmaceutical compositions of the invention are associated with unexpectedly few side effects.

The present invention provides an oral ketotifen pharmaceutical composition adapted for once-a-day administration. It is a unit dosage form and preferably contains 2 milligrams of ketotifen. The pharmaceutical composition is preferably in a matrix form.

The bioavailability of the pharmaceutical compositions of the invention may be measured in conventional manner, e.g. by specific radioimmunoassays to measure the drug concentration in blood plasma.

One radioimmunoassay may be made by conjugating the desmethyl derivative of ketotifen via a Mannich reaction to the free amine groups of bovine serum albumin as protein and polyclonal antibodies are developed from the conjugate in sheep. The typical titre of the resultant antiserum is 1:8000. A radioimmunoassay is developed using ketotifen labelled in the 6 position with tritium. Labelled and unlabelled compound are allowed to compete for the available binding sites on the antibody. At equilibrium free and bound ligand are separated using a dextran coated active charcoal. Total radioactivity of the soluble portion may be measured by liquid scintillation counting.

In another aspect the present invention provides a once-a-day oral pharmaceutical composition comprising ketotifen and on administration providing a mean residence time of ketotifen in plasma of from 24 to 28 hours.

Preferably 2 mg ketotifen is administered. Preferably the mean residence time is from 25 to 27 hours.

The mean residence time (MRT) of an active agent in blood plasma is one recognized method for determining the slowing down of absorption of an active agent, as indicated by for example a delayed onset of the rise of active agent concentration in the blood plasma and/or a decrease in the rate at which the active agent concentration decreases after the peak active agent concentration has been reached.

$$MRT \text{ is } \frac{\int_O^\infty C(t) \cdot t \cdot dt}{\int_O^\infty C(t) \cdot dt}.$$

wherein C(t) is the concentration of active agent in plasma at a time t on the basis of single dose administration trials.

The desired plasma concentrations are preferably analysed with regard to the maximum and minimum active agent concentration (Cmax and Cmin) in steady state bioavailability studies. (either actual—see Example 7 or simulated—see Example 6) relative to corresponding values for reference forms.

In another aspect the present invention provides a once-a-day oral pharmaceutical composition comprising ketotifen which on administration in the steady state provides a $$\frac{Cmax}{Cmin}$$

ratio of from 1.2 to 2.4, for example to 2.3.

Preferably the Cmax/Cmin ratio is from 1.4 to 2.0.

The plasma concentrations may be compared to conventional forms of ketotifen to be administered twice-a-day, e.g. tablets and/or capsules. These are administered in steady state bioavailability trials every 12 hours using half the daily ketotifen dose.

The Cmax and Cmin values may be compared for the pharmaceutical compositions tested. Preferably the relative Cmax is from 0.5 to 1.3, especially 0.7 to 1.1. Preferably the relative Cmin is from 0.6 to 1.3, e.g. to 1:1.

If desired the relative bioavailability compared to a conventional form may be determined in the form of a quotient, e.g.

$$\frac{AUC \text{ per mg dose (retard composition)}}{AUC \text{ per mg dose (reference form)}}.$$

wherein AUC is the Area under the curve extrapolated to infinity, e.g. by measuring from 0 to 33 hours and then extrapolating Further (see example 5) in the case of a single dose or from 0 to 24 hours in the case of a steady state trial.

Preferably the relative bioavailability is from 70 to 25 per cent, especially 80 to 105 per cent.

We have also found that preferred oral pharmaceutical compositions containing ketotifen may be characterised by their in-vitro release data.

In yet a further aspect there is provided an oral pharmaceutical composition comprising ketotifen having the following in vitro ketotifen release rates, according to the rotating basket method at 120 rpm at 37° C. in 500 ml 0.1N HCl changed to pH 6.8 after 120 minutes:

5 to 20 per cent after 15 minutes
10 to 25 per cent after 30 minutes
15 to 40 per cent after 60 minutes
25 to 60 per cent after 120 minutes, e.g.35–50%
35 to 70 per cent after 180 minutes
40 to 75 per cent after 240 minutes.
45 to 80 per cent after 300 minutes In another aspect there is provided an oral pharmaceutical composition comprising ketotifen having the following in vitro ketotifen release rates, according to the rotating paddle method at 50 rpm at 37° C. in 500 ml distilled water;

10 to 30 per cent after 120 minutes
20 to 50 per cent after 240 minutes
30 to 60 per cent after 360 minutes
40 to 75 per cent after 480 minutes
55 to 90 per cent after 720 minutes
70 to 95 per cent after 960 minutes
80 to 100 per cent after 1440 minutes.

In a further aspect there is provided an oral pharmaceutical composition comprising ketotifen having the following in vitro ketotifen release rates according to the rotating paddle method at 120 rpm at 37° C. in 500 ml 0.1N HCl changed to pH 6.8 after 120 minutes:

10 to 20 per cent after 15 minutes
15 to 25 per cent after 30 minutes
25 to 35 per cent after 60 minutes
35 to 50 per cent after 120 minutes
40 to 55 per cent after 150 minutes
45 to 60 per cent after 180 minutes The first 2 sets of the above mentioned 3 sets of release rate characteristics are the preferred characteristics. The in vitro release data may be effected according to conventional methods, e.g. those disclosed in the US pharmacopeia XX for the rotating paddle/rotating basket methods. HPLC or ultra-violet spectroscopy may be used to measure the ketotifen released.

The pharmaceutical compositions of the invention may be made up from conventional pharmaceutical excipients, of which at least one excipient acts to retard the release and/or resorption of the ketotifen.

A wide range of pharmaceutical excipients may be employed. Naturally the combination of specific pharmaceutical excipients and the relative amounts present may have to be determined by routine experimentation.

The ketotifen is preferably present in acid addition salt form, especially the hydrogen fumarate. If desired the free base may be used.

In yet a further preferred aspect the invention provides an oral pharmaceutical composition containing ketotifen in a lipophilic material.

In another aspect the present invention provides a process for the production of an oral once-a-day pharmaceutical composition containing ketotifen which comprises mixing, and if desired, granulating ketotifen with a lipophilic material, preferably a fat, and working up into a unit dosage formulation, preferably a tablet composition.

The pharmaceutical compositions may be formulated in conventional manner, e.g. as used to provide sustained release formulations. Granulating and film coating techniques used in the art may be employed.

Preferably the lipophilic material is a fat. Fats which are preferred include cetyl palmitate, and especially glyceryl fatty acid esters such as glyceryl palmitates or stearates.

The fat is preferably a glyceryl palmito-stearate, preferably ditripalmito stearate. Preferably it contains about 40 per cent full tri-ester palmito-stearic-triglycerides, 45 per cent partial (di)ester palmito-stearic diglycerides, 14 per cent partial monoester stearic monoglyceride and about 1% glycerol. Such a product is commercially available under the tradename Precirol, eogo Precirol A to 5, from Gattefosse, France.

Preferably the fat is in a matrix. Especially preferred are compositions containing a high amount of fat, e.g. with a ratio of ketotifen to fat from about 1:10 to about 1:30, e.g. 1:20 to 1:25.

The composition may be in unit dosage form. It may conveniently be encapsulated. Preferably it is in a composition suitable for tabletting. For this preferably the ketotifen and fat is in the form of a granulate. Conveniently this granulate contains a diluent, filler or bulking agent, which may regulate the release rate, such as lactose, starch, e.g. corn starch, microcrystalline cellulose etc. If desired iron oxide may be present.

The fat granulate is preferably mixed with a placebo granulate containing agents which aid tabletting. The placebo granulate may also contain an agent which helps provide bulk for the tablet, improves flow of the particles in the tabletting machine and may be used to vary slightly the release characteristics of the ketotifeno. Preferably the placebo granulate contains a filler such as lactose. Alternatives include calcium phosphate and sulphate. Preferably a disintegrant such as starch, especially corn starch, is present. Preferably a binding agent such as polyvinylpyrrolidone is present. The placebo granulate preferably has another binding agent to slow down disintegration of the structure. Examples include cellulose derivatives such as hydroxypropylmethylcellulose or especially ethylcellulose.

The ethylcellulose preferably comprises 2.4 to 2.5 hydroxyl groups per glucose moiety. The ethylcellulose preferably has a viscosity between 4 and 22, preferably 7, cps in a 5 per cent solution.

The tablets may be made in conventional manner. The fat granulate may be made by mixing the components, sieving them, granulating at a slightly elevated temperature, e.g. about 50° C., cooling to about 20° to 40° C., and sieving or grinding the mass. The placebo granulate may for example be made in analogous manner to that described in DOS 2,426,811. The placebo granulate is for example made by mixing the components, sieving, granulating with e.g. ethanol, drying and sieving. The fat and placebo granulates may then be mixed.

To aid the tabletting process the fat granulate and any placebo granulates are preferably coated with an outer lubricant phase. If desired one of the granulates may be coated with at least part of or some of the components of an outer phase before mixing with the other granulate. Further coating to provide the complete outer phase may then be provided. A preferred example of lubricant is magnesium stearate. A glidant may be present. A preferred example of glidant is colloidal silica. The preferred form of silica is amorphous. It is commercially available as Aerosil. If desired hydroxypropyl methylcellulose may be present.

In one preferred embodiment the present invention provides:
- a) a fat granulate comprising ketotifen, lactose and glyceryl palmito-stearate,
- b) a lactose placebo granulate also comprising starch and polyvinylpyrrolidone and optionally ethyl cellulose,
- c) an outer phase comprising magnesium stearate and optionally silica.

Typical weight ratios of fat granulate to placebo granulate are from about 1:0.1 to about 1:1, e.g. 1:0.5 to 0.7. Typical weight ratios of ketotifen to total lactose are from about 1:6 to about 1:40, e.g. 1:20 to 1:40. The outer phase may be from about 0.1 to about 25, e.g. 0.5 to 2, per cent of the total weight.

Tabletting may be effected in conventional manner for the compression of high fat content mixtures. Preferred crushing strengths (hardness coefficients) are from about 15 to 50N, conveniently 20 to 40N.

Typical tablets weigh about 100–200 mg and have a film coating of about 2 mg.

Conveniently the tablets may be coated to improve their appearance, e.g. with a non-enteric coating. This may be for example a cellulose ether, e.g. hydroxypropylmethylcellulose. Other excipients such as silica, titanium oxide, talc, polyethyleneglycol or iron oxide may be present. Such films preferably have no significant effect on the retardation.

The pharmaceutical compositions of the invention may be used in the same indications and in the same manner as the known tablets. The efficacy may be determined in standard clinical trials, e.g. by decreasing the number of asthma attacks. Conveniently the pharmaceutical composition of the invention are given in the mornings or evenings, with a dose of 2 mg ketotifen. Clinical trials show the excellent acceptance of the pharmaceutical compositions, few side effects such as sedation, and good efficacy on once-a-day administration. Furthermore, there seem to be no evidence of significant dose dumping or food interaction from pharmacokinetic trials.

All values herein, e.g. to MRT, refer except where otherwise stated to mean values.

Glyceryl ditripalmitostearate is conveniently brand Precirol preferably Precirol Ato 5 (from Gattefosse, France). Silica is conveniently brand Aerosil 200 (from Degussa, Germany).

Polyvinylpyrrolidone is conveniently brand Plasdone K-29-32. Ethylcellulose is conveniently brand Ethylcellulose N7 cps (Hercules, USA). Hydroxypropyimethylcellulose is conveniently brand Methocel E 5 cps. in the film layer and in the outer phase conveniently brand Methocel K 15M.

Further details of the composition of these components may be obtained from Fiedler H. P., Lexikon der Hilfsstoffe, 2nd Edition, Edito Cantor, Aulendorf, W. Germany.

EXAMPLE 1

Tablets comprising a) a fat granulate of
 2.75* mg ketotifen hydrogen fumarate
 23.50 mg lactose
 2.50 mg corn starch
 0.05 mg iron oxide (red or yellow)
 41.20 mg glyceryl ditripalmitostearate
*corresponding to 2 mg ketotifen in base form, crushing strength 15–40N, thickness 2.5 mm, diameter 7 ram.

b) a placebo granulate of
 35.54 mg lactose
 1.33 mg corn starch
 2.33 mg polyivinylpyrro lidone
 0.40 mg ethylcellulose c) an outer phase of
 0.20 mg silica
 0.20 mg magnesium stearate Further examples hereinafter refer to the above composition. If desired the 41.20 mg glyceryl ditripalmitqstearate may be replaced by 30 mg glyceryl ditripalmitostearate.

EXAMPLE 2

Tablets comprising a) a fat granulate of
 2.75 mg ketotifen hydrogen fumarate
 26.0 mg microcrystalline cellulose
 0.05 mg iron oxide (red or yellow)
 41.20 mg glyceryl ditripalmitostearate b) a placebo granulate of
 12.45 mg lactose
 0.45 mg corn starch
 1.00 mg polyvinylpyrrolidone
 0.70 mg ethylcellulose and c) an outer phase of 0.20 mg silica
25.0 mg hydroxypropyl methylcellulose
0.20 mg magnesium stearate Weight 110 mg, crushing strength 30–40N, thickness 2.5 mm, diameter 7 mm.

EXAMPLE 3

Tablets comprising a) a fat granulate of
  2.75 mg ketotifen hydrogen fumarate
  31.5 mg microcrystalline cellulose
  0.05 mg iron oxide (red or yellow)
  35.7 mg glyceryl ditripalmitostearate
b) a placebo granulate of
  57.0 mg lactose
  7.0 mg corn starch
  5.5 mg polyvinylpyrrolidone and
c) an outer phase of
  0.5 mg magnesium stearate.

Weight 140 mg, crushing strength 40–50N, thickness 2.8 mm, diameter 7 mm.

The tablets of examples 1 to 3 may be coated in conventional manner with a film comprising:

|  | Parts by weight |
| --- | --- |
| Hydroxypropyl methylcellulose | 0.250 |
| Titanium dioxide | 0.0475 |
| Talc | 0.025 |
| Iron oxide | 0.006 |

EXAMPLE 4

In vitro and in vivo release

The in vitro release rate of ketotifen from a tablet of Example 1 may be determined according to the rotating paddle method (USP XX) at 120 rpm in 500 ml HCl 0.1N at 37° C.

After 120 minutes the pH is changed to 6. by the addition of a buffer.

Figure 1:
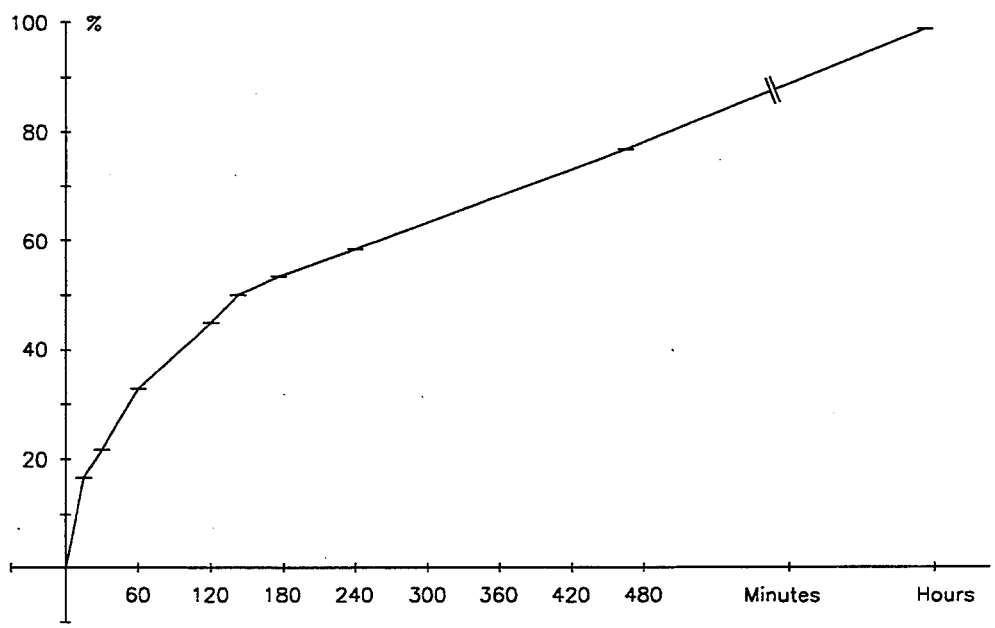
FIG. 1 shows the in vitro release rate (%/time) of a ketotlfen tablet prepared in Ex. 1.

The release rates may be:
10 to 20 per cent after 15 minutes
15 to 25 per cent after 30 minutes
25 to 35 per cent after 60 minutes
35 to 50 per cent after 120 minutes
40 to 55 per cent after 150 minutes
45 to 60 per cent after 180 minutes According to the rotating basket method effected under the same conditions* the example 1 had release rates of for example:
16 per cent after 15 minutes
22 per cent after 30 minutes
32 per cent after 60 minutes
46 per cent after 120 minutes
55 per cent after 180 minutes
59 per cent after 240 minutes
64 per cent after 300 minutes
79 per cent after 480 minutes a representative release rate is given in the accompanying FIG. 1. ,6 *with pH change to 6.8

The in vivo release from two tablets corresponding to 5.50 mg ketotifen hydrogen fumarate administered to 8 healthy patients (4 females and 4 males) who had taken two pharmaceutical compositions according to the invention 10 minutes before breakfast was determined.

The drug level in plasma is followed over 48 hours by taking 12 samples of blood.

Figure 2:
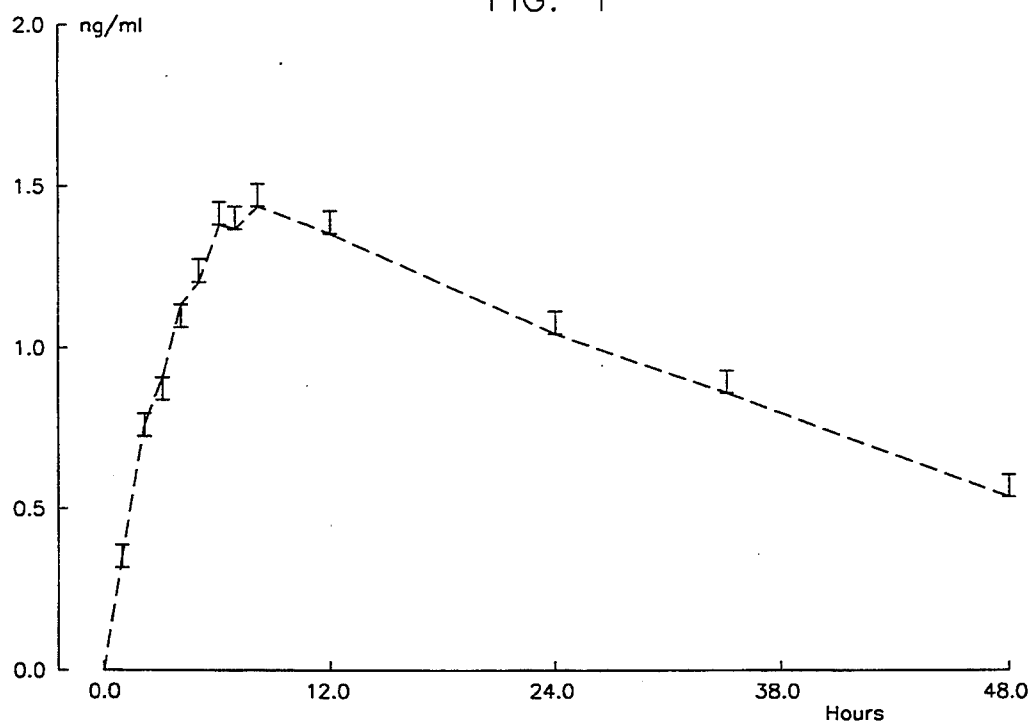
FIG. 2 shows the average profile (ng/ml/hr) of the level of ketotifen in plasma from 8 patients administered two tablets corresponding to 5.50 mg ketotlfen hydrogen fumarate.

The levels give an average profile according to FIG. 2. The kinetic profile is similar to that given in Example 5.

EXAMPLE 5

Determination of relative Bioavailability

Unfilmed retard tablets of examples 1, 2 and 3 were compared with a non-retarded reference capsule of the following composition:

| Ketotifen hydrogen fumarate | 1.38 mg* |
| --- | --- |
| Silica | 0.30 mg |
| Magnesium stearate | 1.40 mg |
| Corn starch | 56.00 mg |
| Mannitol | 80.92 mg |
| | 140.00 mg |

*corresponding to 1 mg free base

In a first study the tablets of example 3 are compared with the reference capsule in 9 healthy volunteers and the plasma profile of both forms measured at regular intervals.

In a second study the tablets of examples 1 and 2 are tested in 8 healthy subjects under similar conditions to that in the first study. The plasma profile is determined.

The plasma profiles of the reference capsules and the tablets of examples 1 and 2 are followed for 33 hours and for the tablets of example 3 for 28 hours.

For the retard forms a single dose of 2 tablets (=4 mg ketotifen base) and for the reference forms of 2 capsules (=2 mg ketotifen base) were administered. The plasma concentration of the reference was doubled for the comparison.

Figure 3:
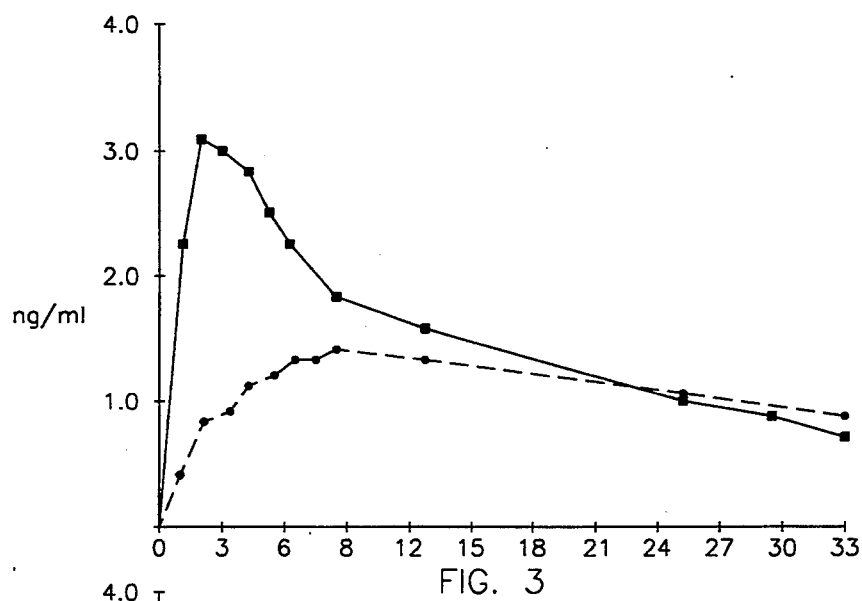
FIG. 3 shows the average profile (dotted fine) of the level of ketotifen in plasma from 8 patients given 2 tablets from Ex. 1 containing a total of 4 mg ketotifen base compared to the doubled average profile (solid line) for a reference form of 2 capsules containing a total of 2 mg ketotifen base.
Figure 4:
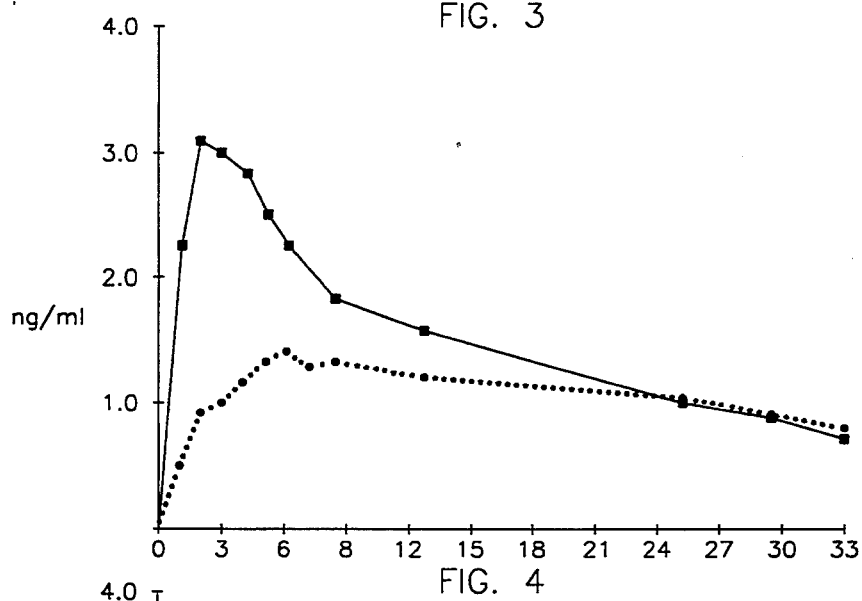
FIG. 4 shows the average profile (dotted line) of the level of ketotifen in plasma from 8 patients given 2 tablets from Ex. 2 containing a total of 4 mg ketotifen base compared to the doubled average profile (solid line) for a reference form of 2 capsules containing a total of 2 mg ketotifen base.
Figure 5:
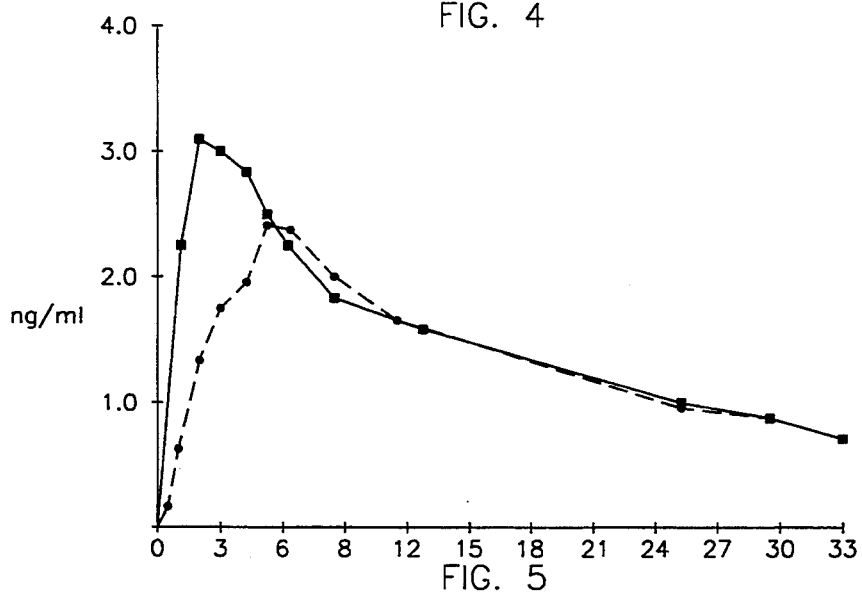
FIG. 5 shows the average profile (dotted line) of the level of ketotifen in plasma from 9 patients given 2 tablets from Ex. 3 containing a total of 4 mg ketotifen base compared to the doubled average profile (solid line) for a reference form of 2 capsules containing a total of 2 mg ketotifen base.

The double value of the references are shown in FIG. 3 with the plasma profile of the tablets of example 1, in FIG. 4 with the plasma profile of tablets of example 2 and in FIG. 5 with the plasma profile of tablets of example 3. (Plasma profiles are in nanograms/ml versus the time T in hours after administration).

Results:
FIG. 3 (tablets of example 1) Relative bioavailability=85.5%
FIG. 4 (tablets of example 2) Relative bioavailability=85%
FIG. 5 (tablets of example 3) Relative bioavailability=90.1%

The relative bioavailability of the pharmaceutical compositions of the invention is preferably between 70 and 125%, especially between 80 and 105%, more especially up to 88%.

For the calculation of the relative bioavailability the curves are extrapolated to infinity.

EXAMPLE 6

Determination of the average mean-residence time and relative Cmax and Cmin and $$\frac{Cmax}{Cmin}$$

These parameters are obtained from single dose trials and the results simulated to steady state trials over 24 hours using the retarded Example 1 form.

Figure 7:
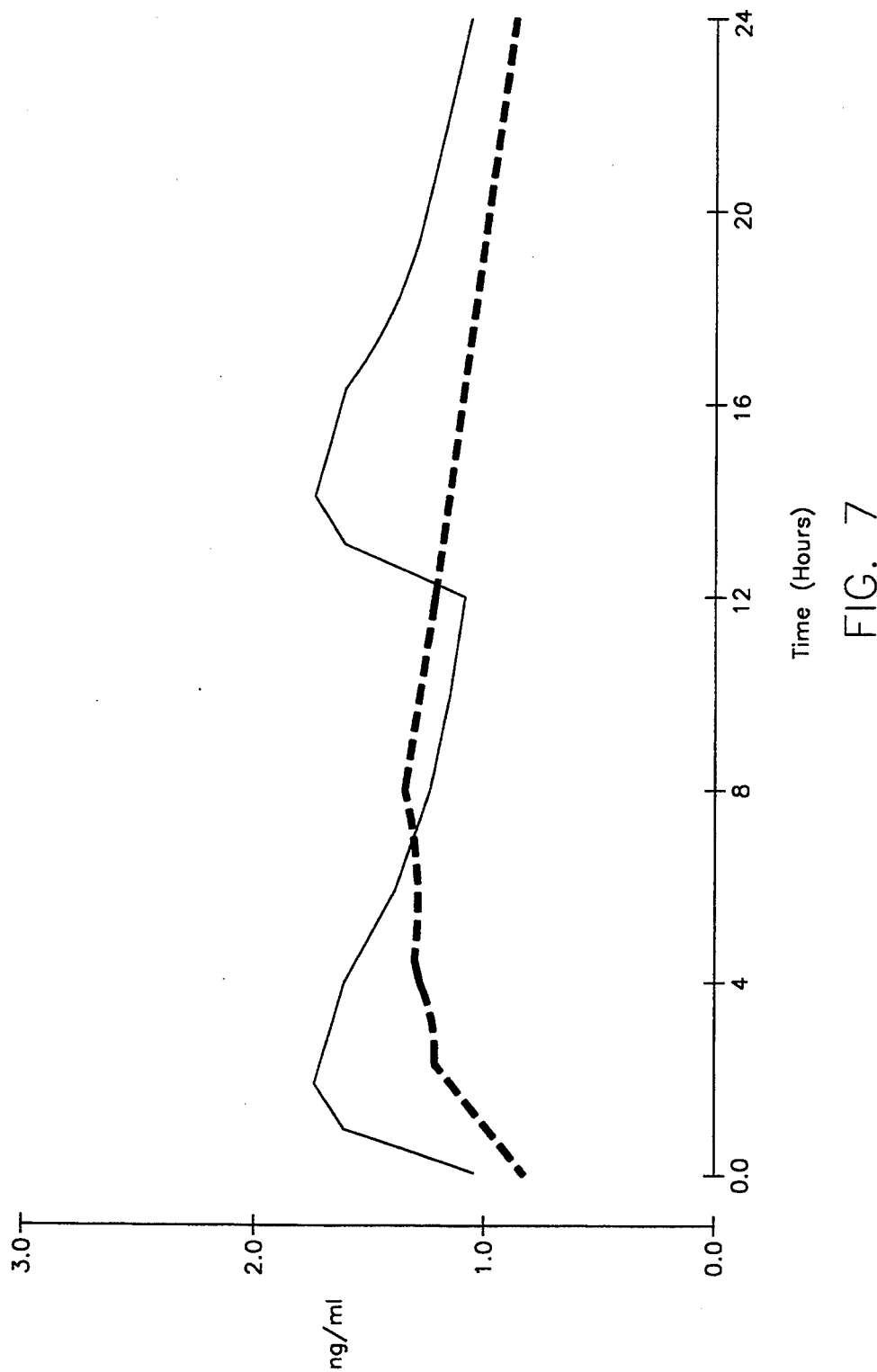
Figure 8:
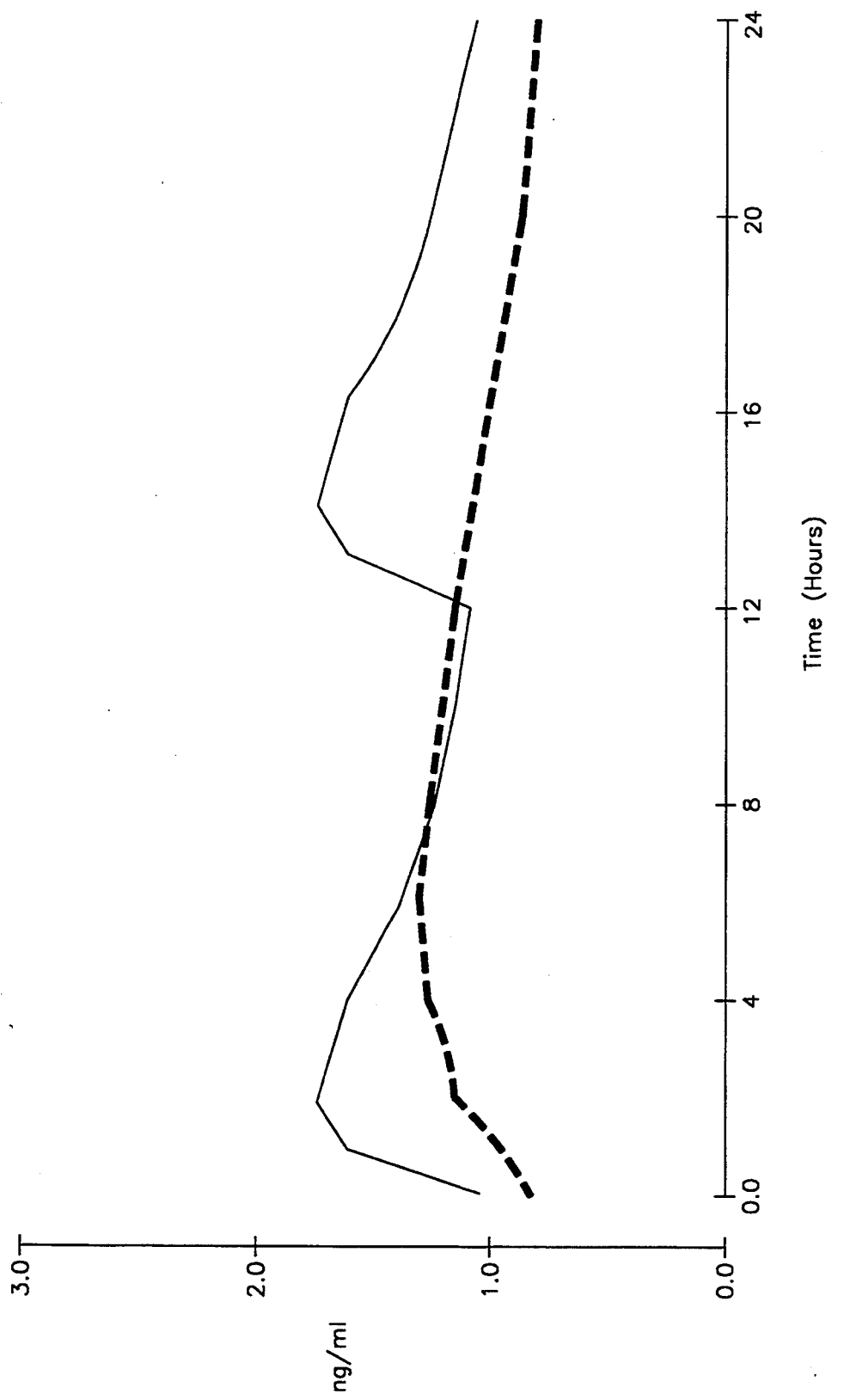
Figure 9:
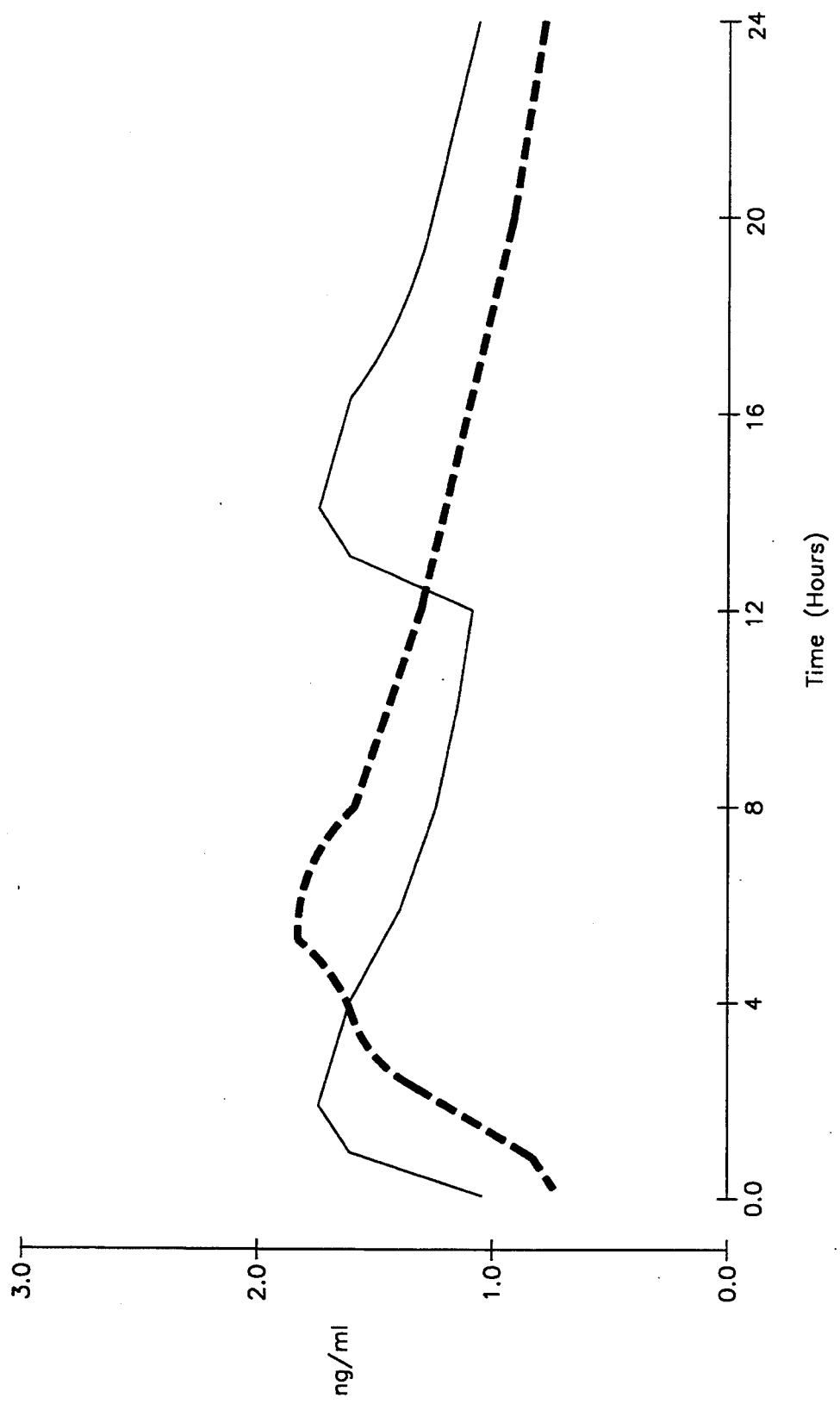

In this trial the plasma curve of a retarded single daily dose of 2.75 mg ketotifen hydrogen fumarate (=2 mg base) is determined over 2 hours, and compared with the plasma curve of one unit dose of a non-retarded reference form and measured over 12 hours.(In FIGS. 7, 8 and 9, the dotted plasma curve is compared with the reference curve from 0 to 12 hours which in the figures is simulated for the second time interval from 12 to 24 hours).

Figure 6:
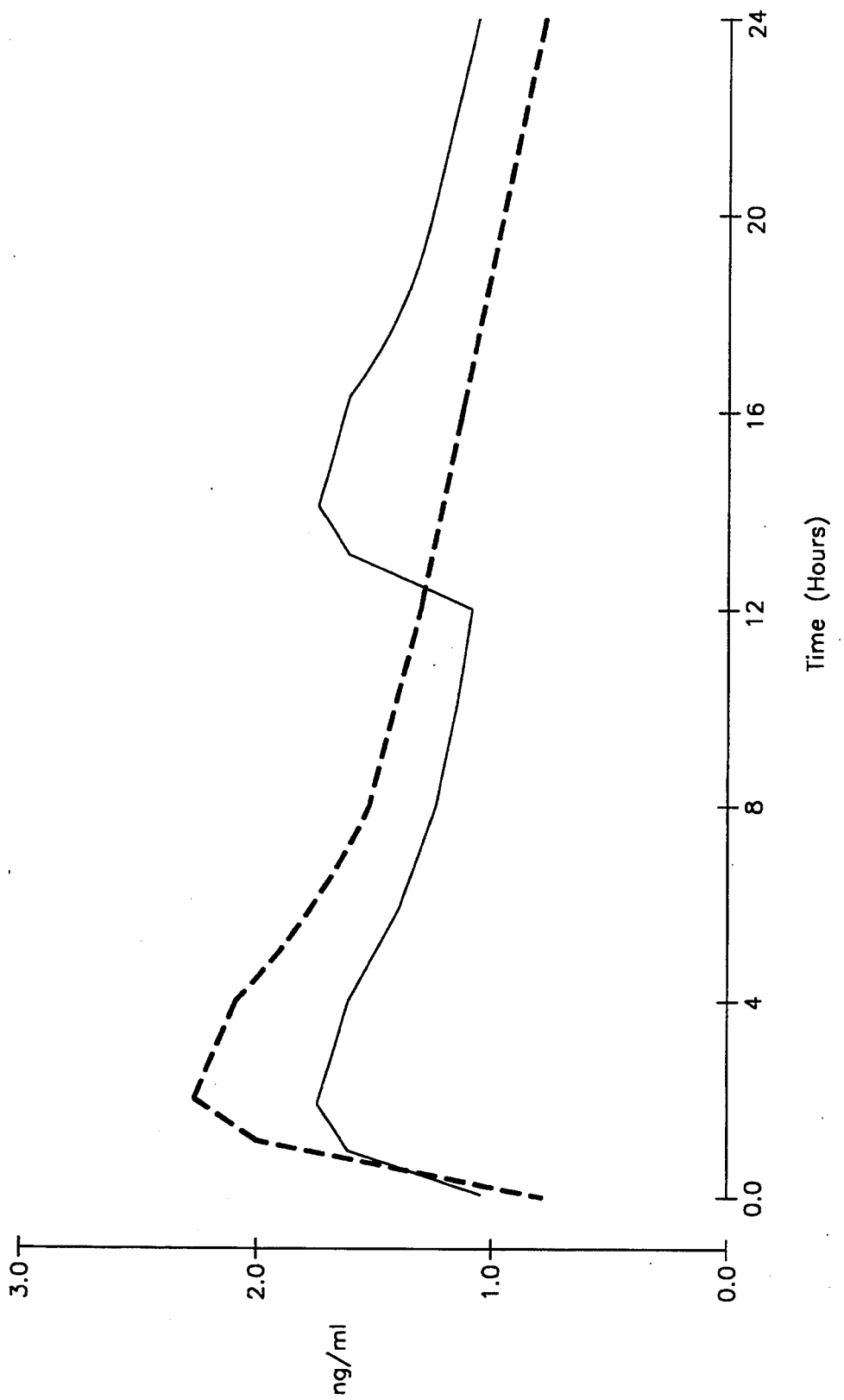
FIGS. 6, 7, 8 and 9 show the profile (dotted line) of the level of ketotifen In plasma from 4 individual patients, respectively, given a single tablet from Ex. 1 containing a total of 2 mg ketotifen base compared to the profile (solid line) for a non-retarded reference form containing a total of 2 mg ketotifen base each administered at 0 hours and 12 hours.

In FIG. 6 as a comparison (dotted line) a non-retarded tablet of 2.75 mg ketotifen hydrogen fumarate (=2 mg base) after a single dose is measured for 24 hours and compared with the plasma curve of a unit dose of non-retarded reference form after two single administrations at time zero and at the time 12 hours respectively.

From the profiles shown in FIGS. 6,7,8 and 9 the following results are obtained:

|  | FIG. 6<br>Ref. Form<br>1 mg Base =<br>1 caps.<br>2 × pro day | FIG. 6<br>Ref. Form<br>2 mg Base =<br>2 caps.<br>1 × pro day | FIG. 7<br>Ex. 1<br>2 mg Base =<br>1 Tabl.<br>1 × pro d. | FIG. 8<br>Ex. 2<br>2 mg Base =<br>1 Tabl.<br>1 × pro d. | FIG. 9<br>Ex. 3<br>2 mg Base =<br>1 Tabl<br>1 × pro d. |
|---|---|---|---|---|---|
| Mean residence time | 22.4 | | 26 | 26 | |
| C max Retard form | 1 | 1.31 | 0.78 | 0.77 | 1.05 |
| C max Reference f. | | | | | |
| C min Retard form | 1 | 0.77 | 0.80 | 0.79 | 0.73 |
| C min Reference f. | | | | | |
| C max | 1.7 | 2.8 | 1.6 | 1.6 | 2.4 |
| C min | | | | | |

In general the mean residence time in plasma is from 24 to 29, and especially 25 to 28, hours for a pharmaceutical composition of the invention.

The relative Cmax after a single daily oral administration is especially 0.5 to 1.3, e.g. 0.7 to 1.1, the relative Cmin especially 0.6 to 1.3, e.g. 0.6 to 1.1 and $$\frac{Cmax}{Cmin}$$

especially 1.2 to 2.3, e.g. 1.4 to 2.0, based on the non-retarded form, and over a 12 hour interval for a half daily dose.

EXAMPLE 7

Figure 10:
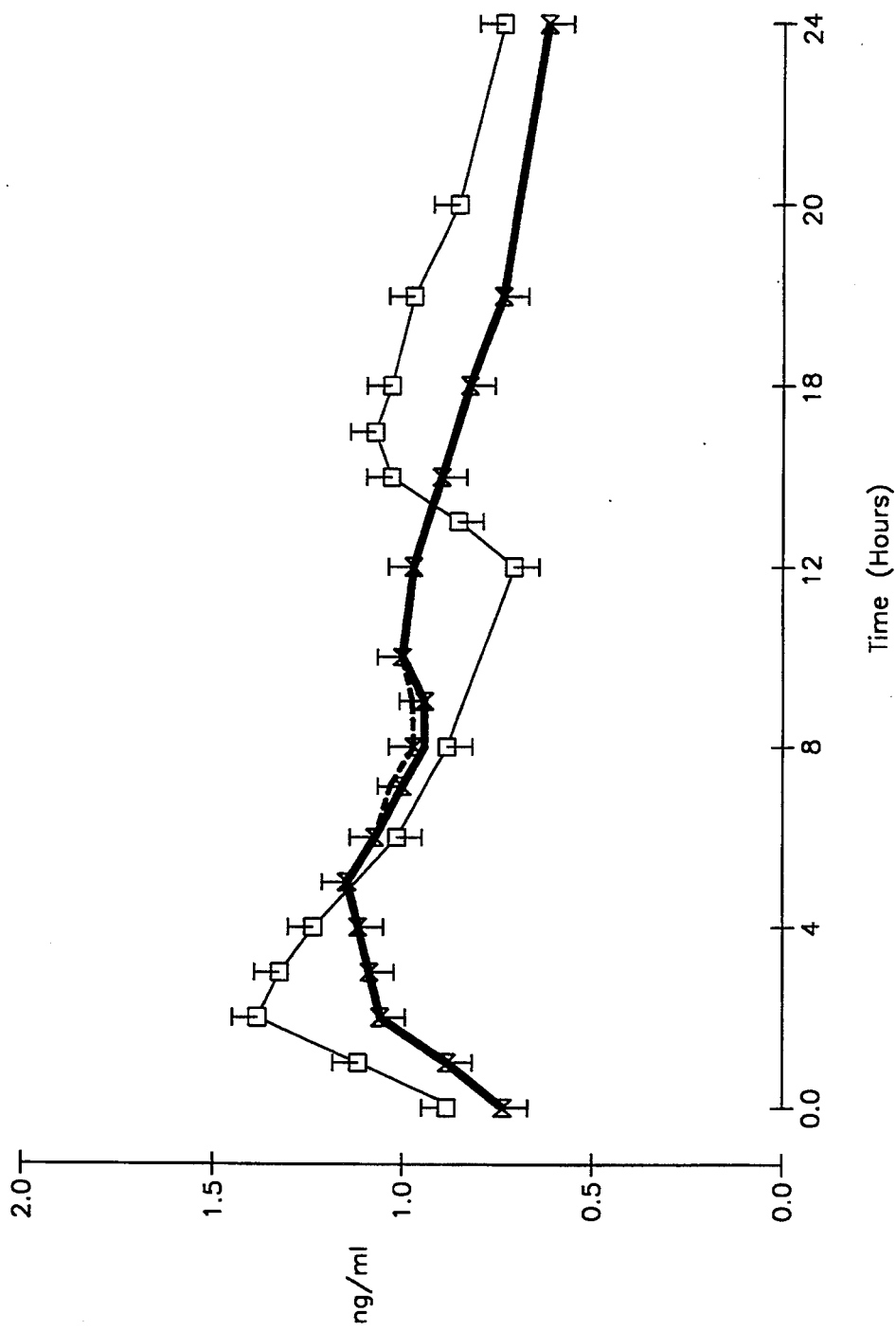
FIG. 10 shows the average profile (bold line), of the level of ketotifen in plasma from 12 patients given tablets from Ex. 1 compared to the profile (unbold line) for a non-retarded reference form given at 0 hours and 12 hours later.

Analogous to Example 6 a full steady state trial with 12 healthy subjects with the retarded tablets of example 1 (given in the morning), and the reference form described in example 5, given in the morning and 12 hours later, was effected. The results are shown in FIG. 10.

The difference to the trial in example 6 resides in the fact that the profile of the retard formulation (thick line) is derived from the seventh day onwards and no extrapolation is made. The second curve is derived from the reference forms.

In this steady state trial the relative bioavailability of the pharmaceutical composition of the invention was 93% (based on the AUC from 0 to 24 hours). The relative ratios of the $C_{max}$ was 83% based on day 7, $C_{min}$ (based on day 7) 84% and the ratio of $C_{max}$ to $C_{min}$ was 1.63 for the composition of the invention compared to 1.65 for the reference.

EXAMPLE 8

Tablet production

| Ingredient | Weight (mg) |
|---|---|
| Fat granular | |
| Ketotifen hydrogen fumarate | 2.75 |
| Lactose (200 mesh) | 23.55 |
| Corn starch | 2.5 |
| Glyceryl ditripalmitostearate | 41.2 |
| Placebo granulate | |
| Lactose (200 mesh) | 35.6 |
| Corn starch | 1.3 |
| Polyvinylpyrrolidone | 2.3 |
| Ethylcellulose | 0.4 |
| Outer phase | |
| Silica | 0.2 |
| Magnesium stearate | 0.2 |
| Film coating | |
| Hydroxypropyl methylcellulose | 1.25 |
| Polyethylene glycol 6000 | 0.125 |
| Titanium oxide | 0.356 |
| Talc | 0.125 |
| Silica | 0.125 |
| Iron oxide yellow | 0.0188 |
| Total weight (112 mg; Core 110 mg, Film coating 2 mg). | |

Fat granulate

The fat granulate is made in 2 batches. The preparation of one batch is as follows:

2.75 kg of ketotifen hydrogen fumarate is mixed with 8.55 kg lactose for 5 minutes. The mass is sieved (vibration sieve; mesh width 500; hole size 250 microns). Separately 15 kg lactose and 2.5 kg corn starch are sieved and mixed (vibration sieve; hole size 1600 microns, wire diameter 630 microns). Glyceryl ditripalmitostearate is sieved (mesh width 1600, hole size 630 microns) and 41.2 kg thereof is mixed with two previously sieved masses, forming ketotifen fat granulate over ca. 30 minutes to ca. 50° C. The fat granulate is cooled to about 20° to 30° C. The mass is broken up using a sieve (hole size 1.5 mm). Total weight (two batches) 140 kg.

Placebo granulate 71.2kg lactose, 2.6 kg corn starch, 4.6 kg polyvinylpyrrolidone and 0.8 kg ethyl cellulose N7 are sieved (vibration sieve mesh width 1600; hole size 630 microns) and mixed for about 2 minutes. 8 kg 94% ethanol are added and the mass granulated. The mass is dried at room temperature of 50° C. (granulate temperature 36° C.). The mass is broken up as for the fat granulate to produce the placebo granulate. Total weight 79.2 kg.

Tabletting composition 0.4 kg silica are mixed with 4 kg of the fat granulate and sieved (mesh width 1000; hole size 400 microns) and the sieved mass is mixed with the rest of the fat granulate. 3 kg of the placebo granulate and 0.4 kg of magnesium stearate are mixed and sieved (mesh width 1000, hole size 400 microns). This mass is mixed with the rest of the placebo granulate, and then with the silica/fat granulate mass. 220 kg mass is sufficient for 2 million tablets.

Tabletting is effected e.g. on a Fette 1000 Perfekta machine to provide tablets of 110 mg weight, 2.8 mm thickness under a pressure of 3–6 kN.

Film coating

A solution of 4.5 kg hydroxypropyl methylcellulose, 0.4 kg polyethylene glycol and 67.5 kg demineralized water is made up 0.18 kg 25% ammonia are added. 8.1 kg demineralized water is added. 1.2825 kg titanium dioxide, 0.45 kg talc, 0.45 kg silica and 0.0675 kg iron oxide yellow are mixed, ground, mixed with 7.02 kg water, and added to the solution to provide a film suspension (98 kg). The tablets are coated with the solution at ca. 35° C. in a coating pan (AccelaCota 48 inches).

In vitro release rates

Release rates measured by the rotating paddle method at 50 rpm at 37° C. in 500 ml distilled water for 6 tablets.

| Time (minutes) | Percent released | SEM |
| --- | --- | --- |
| 120 | 16.0 | 2.7 |
| 240 | 34.5 | 2.4 |
| 360 | 47.3 | 2.9 |
| 480 | 56.3 | 4.8 |
| 600 | 63.5 | 3.7 |
| 720 | 70.9 | 3.1 |
| 960 | 80.5 | 4.8 |
| 1200 | 89.5 | 3.9 |
| 1440 | 92.1 | 3.2 |

Release rates measured by the rotating basket method at 120 rpm at 37° C. in 500 ml 0.1N HCl with a pH change to 6.8 after 2 hours.

| Time (minutes) | Percent released |
| --- | --- |
| 60 | 23 |
| 120 | 34 |
| 150 | 34 |
| 180 | 37 |
| 240 | 41 |
| 300 | 46 |

What we claim is:

1. An oral pharmaceutical composition in the form of a tablet comprising (i) a fat granulate containing from about 2 milligrams to about 5.5 milligrams of ketotifen or acid addition salt thereof in a lipophilic matrix comprising cetyl palmitate or glyceryl fatty acid esters; (ii) a placebo granulate containing lactose and one or more components selected from the group consisting of starch, cellulose ethers and polyvinylpyrrolidone; and (iii) a film coating covering the fat granulate and placebo granulate and said granulates containing an outer lubricant phase comprising magnesium stearate, wherein said film coating comprises 0.1 to 25% by weight based on total weight of said composition and wherein the weight ratio of said fat granulate to said placebo granulate is from about 1:0.1 to about 1:1, the weight ratio of said ketotifen to said lipophilic matrix is 1:10 to about 1:30, and composition is in a unit dosage form for once-a-day oral administration, and all ingredients in said composition are pharmaceutically acceptable.

2. A composition according to claim 1 in which the weight ratio of said ketotifen to said lipophilic matrix is from about 1:20 to 1:25.

3. A composition according to claim 1 in which said lipophilic matrix is a glycerol fatty acid ester.

4. A composition according to claim 1 containing from about 2 milligrams to about 4 milligrams of ketotifen.

5. A composition according to claim 3 in which said glycerol fatty acid ester is a glyceryl palmito-stearate.

6. A composition according to claim 1 containing from about 2 milligrams to about 2.75 milligrams of ketotifen or acid addition salt thereof.

7. A composition according to claim 1 containing about 2 milligrams of ketotifen.

8. A composition according to claim 1 containing about 2.75 milligrams of ketotifen hydrogen fumarate.—

* * * * *